United States Patent
Park et al.

(10) Patent No.: US 8,720,252 B2
(45) Date of Patent: May 13, 2014

(54) QUALITY CONTROL APPARATUS FOR GAS DIFFUSION LAYER FOR FUEL CELLS

(75) Inventors: Gu-Gon Park, Daejeon (KR); Minjin Kim, Daejeon (KR); Young-Jun Sohn, Daejeon (KR); Young-Woo Choi, Cheongju-si (KR); Seok-Hee Park, Daejeon (KR); Sung-Dae Yim, Daejeon (KR); Tae-Hyun Yang, Daejeon (KR); Young-Gi Yoon, Daejeon (KR); Won-Yong Lee, Daejeon (KR); Chang-Soo Kim, Incheon (KR)

(73) Assignee: Korea Institute of Energy Research, Daejeon (KR)

( * ) Notice: Subject to any disclaimer, the term of this patent is extended or adjusted under 35 U.S.C. 154(b) by 727 days.

(21) Appl. No.: 12/906,669

(22) Filed: Oct. 18, 2010

(65) Prior Publication Data

US 2011/0271742 A1    Nov. 10, 2011

(30) Foreign Application Priority Data

May 4, 2010 (KR) .......................... 10-2010-0041764

(51) Int. Cl.
*G01N 15/08* (2006.01)

(52) U.S. Cl.
USPC ............................................................ 73/38

(58) Field of Classification Search
CPC .............. G01N 15/08; G01N 15/0806; G01N 2015/08; G01N 2015/084; G01N 2015/086
USPC ............................................................. 73/38
See application file for complete search history.

(56) References Cited

U.S. PATENT DOCUMENTS

| | | | | |
|---|---|---|---|---|
| 5,381,713 A | * | 1/1995 | Smith | 83/881 |
| 2010/0236335 A1 | * | 9/2010 | Park et al. | 73/818 |

FOREIGN PATENT DOCUMENTS

KR    100902316 B1    6/2009

* cited by examiner

*Primary Examiner* — Daniel S Larkin
(74) *Attorney, Agent, or Firm* — The Webb Law Firm

(57) ABSTRACT

A quality control apparatus for a gas diffusion layer includes a support, at least one first pressure device, a plate provided below the first pressure device and supporting the pressure applied to the gas diffusion layer sample, a first controller controlling the compression of the first pressure device, a thickness gauge measuring the thickness of the gas diffusion layer sample, a flow channel formed in the sample compressing portion to discharge a gas to the gas diffusion layer sample, a gas supply controller, a gas supply source, a pressure gauge, two fixing devices, a third controller controlling the compression of the fixing devices, two second pressure, a second controller controlling the compression of the second pressure device, a stopper, a protrusion, and a load cell.

4 Claims, 3 Drawing Sheets under the compression pressure of the first pressure device, which the existing apparatus does not have. That is to say, the applicable inspection items can be extended and diverse evaluation results can be provided.

QUALITY CONTROL APPARATUS FOR GAS DIFFUSION LAYER FOR FUEL CELLS

CROSS-REFERENCE TO RELATED APPLICATIONS

This application claims priority under 35 U.S.C. §119 to Korean Patent Application No. 10-2010-0041764, filed on May 4, 2010 in the Korean Intellectual Property Office, the disclosure of which is incorporated herein by reference in its entirety.

TECHNICAL FIELD

The following disclosure relates to an apparatus capable of monitoring various physical quantities of a gas diffusion layer employed in a fuel cell in short time in a non-destructive manner. More particularly, it relates to an apparatus capable of monitoring thickness, in-plane permeability, bending stiffness, or the like of a gas diffusion layer in short time in a non-destructive manner for a preliminary quality control in a mass production process of a fuel cell.

BACKGROUND

A fuel cell is a power generation system that converts chemical energy of a fuel and an oxidant into electrical energy. The fuel is typically a hydrocarbon such as hydrogen, methanol, butane, etc., and the oxidant is typically oxygen. The fuel cells are divided into phosphoric acid fuel cells, molten carbonate fuel cells, solid oxide fuel cells, polymer electrolyte membrane fuel cells, alkaline fuel cells, or the like. Although these fuel cells operate based on the same principle, they are different in the fuel used, operation temperature, catalyst, electrolyte, and so forth.

In a fuel cell, a membrane electrode assembly (MEA) is the most basic unit that generates electricity and consists of an electrolyte membrane and an anode and a cathode respectively formed at either side of the electrolyte membrane.

Typically, a polymer electrolyte membrane fuel cell consists of a membrane electrode assembly comprising an electrolyte membrane sandwiched between an anode (also called "fuel electrode" or "oxidation electrode") and a cathode (also called "air electrode" or "reduction electrode"), gas diffusion layers and separators for forming a stack.

A fuel cell stack is formed by stacking tens or hundreds of unit cells where electrochemical reaction occurs. Both end plates of the unit cell or the stack are compressed by a tie rod or pressurized air in order to reduce contact resistance between components. The end plates are provided with inlet and outlet ports for a reaction gas, circulation ports for cooling water, and connectors for electric power output.

The separator is provided with a flow channel, which supplies the fuel to the anode and oxygen to the cathode, and also serves to connect the anode and the cathode of each membrane electrode assembly in series.

Electrochemical oxidation of the fuel occurs at the anode, while electrochemical reduction of oxygen occurs at the cathode. In the process, electricity is generated by the movement of electrons and heat and water are produced.

At the gas diffusion layer, diffusion of the fuel, oxygen and water occurs. Also, electrons produced in a catalyst layer are transferred by the gas diffusion layer. The gas diffusion layer is generally made of a conductive carbon material. Typically, the gas diffusion layer is made of carbon fiber, carbon cloth, carbon paper or carbon felt. Further, the gas diffusion layer of a fuel cell may further comprise a microporous layer (MPL) coated thereon. Usually, the microporous layer is made of graphite, carbon nanotube (CNT), vulcan, Ketjen black, carbon black, or the like.

The basic physical properties of the gas diffusion layer, i.e., thickness, contact resistance, gas permeability, bending stiffness, etc., are also important in the designing and manufacturing of the fuel cell stack. Individual apparatuses for measuring each of the basic physical properties are available. Also, the apparatus for evaluating the physical properties of the gas diffusion layer disclosed in Korean Patent No. 10-0902316, which was filed by the present inventors, is useful in evaluating major basic physical properties of the gas diffusion layer simultaneously under various conditions.

However, when considering mass production, the aforesaid apparatus is problematic in that, although the precision is good, a considerable amount of time is required for the evaluation. Since the degree of compression has to be changed for individual samples and the flow rate and pressure difference are evaluated for each sample, 1 to 3 hours may be required for the evaluation of one sample. It is needless to say that much more time is required when different apparatuses are used to measure the different physical properties of the gas diffusion layer.

Further, since the physical property measuring apparatus performs destructive inspection, i.e. since it requires that the gas diffusion layer in the form of a sheet or roll be broken or separated for the inspection, the gas diffusion layer cannot be used to manufacture a fuel cell after the evaluation. For an automated fuel cell stack manufacturing process, an apparatus for quality control of the gas diffusion layer should satisfy the requirements of "non-destructive inspection" and "completion of inspection in short time". But, there is no available apparatus that satisfies them.

SUMMARY

The present invention is directed to providing an apparatus capable of measuring core physical properties of a gas diffusion layer that greatly affect the performance of a fuel cell in a non-destructive manner by total inspection. The present invention is also directed to providing an apparatus capable of remarkably reducing the measuring time as compared to the existing apparatus.

More particularly, the present invention is directed to providing an apparatus capable of measuring thickness and pressure difference, which is required to calculate in-plane permeability, of a gas diffusion layer while the gas diffusion layer is compressed with a predetermined pressure. Further, the present invention is directed to providing a quality control apparatus for a gas diffusion layer capable of measuring bending stiffness of a gas diffusion layer sample along two perpendicular directions in a non-destructive manner.

In one general aspect, the present invention provides a quality control apparatus for a gas diffusion layer, comprising: a support; at least one first pressure device provided at the support and comprising a sample compressing portion compressing a gas diffusion layer sample therebelow; a plate provided below the first pressure device and supporting the pressure applied to the gas diffusion layer sample; a first controller connected to the first pressure device and controlling the compression of the first pressure device; a thickness gauge attached on one side of the first pressure device and measuring the thickness of the gas diffusion layer sample; a flow channel formed in the sample compressing portion to discharge a gas to the gas diffusion layer sample; a gas supply controller connected to the flow channel and controlling to continuously supply the gas to the flow channel at a predetermined flow rate; a connector connecting the flow channel and the gas supply controller; a gas supply source connected to the gas supply controller and supplying the gas to the flow channel; and a pressure gauge provided near the inlet of the flow channel and measuring the input pressure of the gas diffusion layer sample.

The sample compressing portion moves downward under the control of the first controller and compresses the gas diffusion layer sample placed on the plate, and the inlet of the flow channel is formed on the upper surface or side surface of the sample compressing portion and the outlet of the flow channel is formed on the bottom surface of the sample compressing portion to discharge the gas to the gas diffusion layer sample. Accordingly, the thickness gauge measures the thickness of the gas diffusion layer sample while the gas diffusion layer sample is compressed with a predetermined pressure, and the pressure gauge measures the pressure of the gas supplied to the gas diffusion layer sample.

The first pressure device may comprise a first pneumatic cylinder provided at the support and the sample compressing portion, which is connected to a piston rod of the first pneumatic cylinder and moves downward as the first pneumatic cylinder is compressed to compress the gas diffusion layer sample therebelow, the first controller may be a variable pressure regulator connected to the first pneumatic cylinder and controlling the air pressure of the first pneumatic cylinder, and the thickness gauge may be attached below the first pneumatic cylinder and measure the thickness of the gas diffusion layer sample.

The connector may be a hose one end of which is connected to the inlet of the flow channel, and the gas supply controller may be a variable flow rate regulator provided at the other end of the hose and controlling to continuously supply the gas to the flow channel at a predetermined flow rate.

The quality control apparatus for a gas diffusion layer may further comprise: two fixing devices provided respectively along transverse and longitudinal directions at the support and fixing the gas diffusion layer sample therebelow by compressing; a third controller connected to the fixing devices and controlling the compression of the fixing devices; two second pressure devices provided at the support and comprising rods compressing the end portions of the gas diffusion layer sample; a second controller connected to the second pressure device and controlling the compression of the second pressure device; a stopper provided at a stopper support provided at the support and restricting the second pressure device so as to compress the gas diffusion layer sample within a predetermined angle; a protrusion provided at the second pressure device and restricting the downward movement of the second pressure device along with the stopper; and a load cell fixed on the rod and measuring a force applied to the rod.

The fixing device along the transverse direction may comprise a fixing portion which moves downward as it is compressed and fixes the gas diffusion layer sample by compressing it in the transverse direction, and the fixing device along the longitudinal direction may comprise a fixing portion which moves downward as it is compressed and fixes the gas diffusion layer sample by compressing it in the longitudinal direction. The fixing of the gas diffusion layer sample by the fixing portion may be accomplished by supporting of the plate, one rod of the two second pressure devices may be aligned in parallel with the fixing portion in the transverse direction on the plate, and the other rod of the two second pressure devices may be aligned in parallel with the fixing portion in the longitudinal direction on the plate. The rods of the second pressure device may move downward as they are compressed so that the gas diffusion layer sample is bent within a predetermined angle so as to measure the bending stiffness of the gas diffusion layer sample in the transverse and longitudinal directions.

The fixing device may comprise a third pneumatic cylinder provided at the support and the fixing portion having a shape of a long rod, which is arranged in the transverse or longitudinal direction at the edge portion of the plate, is connected to a piston rod of the third pneumatic cylinder, and moves downward as the third pneumatic cylinder is compressed to fix the gas diffusion layer sample by compressing.

The second pressure device may comprise a second pneumatic cylinder provided at the support and a rod which is connected to a piston rod of the second pneumatic cylinder and moves downward as the second pneumatic cylinder is compressed to compress the edge portion the gas diffusion layer sample.

The quality control apparatus for a gas diffusion layer may further comprise a central controller electrically connected to the first controller, the gas supply controller, the second controller, the third controller, the thickness gauge, the pressure gauge and the load cell.

The central controller may control the compression of the first pressure device, the flow rate of the gas permeating the gas diffusion layer sample, the fixing of the fixing device and the force applied to the rod of the second pressure device.

The central controller may also classify the gas diffusion layer sample depending on the thickness of the gas diffusion layer sample measured by the thickness gauge, compute the in-plane permeability from the pressure measured by the pressure gauge, and display the bending stiffness of the gas diffusion layer sample by receiving an electrical signal from the load cell.

The quality control apparatus for a gas diffusion layer of the present invention is capable of measuring the thickness, gas permeability and bending stiffness of the gas diffusion layer sample in short time in a non-destructive manner. The overall measuring time may be within 10 to 30seconds, from measurement to computation, although it may vary depending on the measuring condition.

The quality control apparatus for a gas diffusion layer of the present invention is useful for quality inspection of the gas diffusion layer in a mass production process of a fuel cell, and allows monitoring of thickness, gas permeability and bending stiffness of the gas diffusion layer sample in short time in a non-destructive manner. Accordingly, if the apparatus of the present invention is used in a mass production process of a fuel cell, the gas diffusion layer failing to satisfy the quality standard may be excluded when assembling a fuel cell stack and, thus, the quality of the fuel cell may be improved.

Other features and aspects will be apparent from the following detailed description, the drawings, and the claims.

DETAILED DESCRIPTION OF EMBODIMENTS

Figure 1:
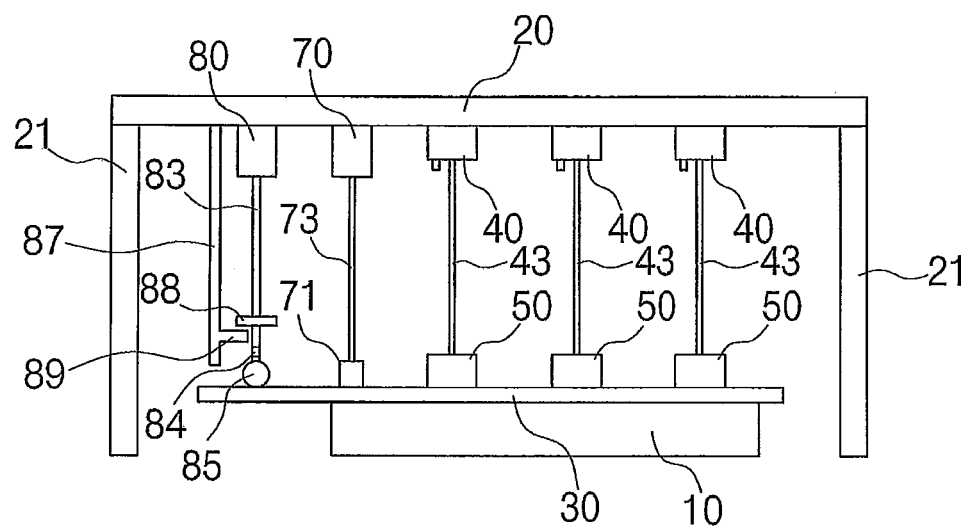
FIG. 1 is a schematic front view of a quality control apparatus for a gas diffusion layer according to an embodiment of the present invention.

The advantages, features and aspects of the present invention will become apparent from the following description of the embodiments with reference to the accompanying drawings, which is set forth hereinafter. The present invention may, however, be embodied in different forms and should not be construed as limited to the embodiments set forth herein. Rather, these embodiments are provided so that this disclosure will be thorough and complete, and will fully convey the scope of the present invention to those skilled in the art. The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

A gas diffusion layer is a component of a fuel cell such as a direct methanol fuel cell (DMFC), a phosphoric acid fuel cell (PAFC), a polymer electrolyte membrane fuel cell (PEFC), or the like. It plays an important role in the performance of a fuel cell of transferring electrons, as well as diffusion of oxygen and water.

However, a commercially available gas diffusion layer has a thickness in a range of about 400 μm±50 μm. As such, since even the same product has nonuniform quality, total inspection of major physical properties of the gas diffusion layer is necessary during the production of a fuel cell. To describe in more detail, let's take an example of a fuel cell used in vehicles, consisting of about 400 unit cells. Since two gas diffusion layers are used for each unit cell, if an error of each gas diffusion layer is 25 μm in one direction, the unit cell has an error of 50 μm. Thus, a fuel cell stack formed by stacking of 400 unit cells amounts to 2 cm. Such a large error may be fatal to the quality of the fuel cell.

Accordingly, total inspection of the gas diffusion layer is necessary during the production process of a fuel cell. For the inspected gas diffusion layer to be used for the production of a fuel cell, the inspection should be non-destructive. Further, for a mass production process, it is required that a large number of gas diffusion layers could be inspected in short time.

The present invention provides an apparatus capable of measuring physical properties of the gas diffusion layer in a non-destructive manner by total inspection in a mass production process of a fuel cell.

The present invention provides an apparatus capable of measuring core physical properties of the gas diffusion layer that greatly affect the performance of a fuel cell. As the core physical properties that greatly affect the uniformity and reproducibility of the fuel cell stack, thickness, in-plane permeability and bending stiffness were selected.

In-plane permeability refers to a permeability of a gas through a gas diffusion layer sample along a direction parallel with the gas diffusion layer sample. It is an important physical property value of the gas diffusion layer and is especially important in predicting bypass flow to the gas diffusion layer when designing the separator or performing computer simulation.

The present invention provides a quality control apparatus for a gas diffusion layer capable of measuring flow rate and pressure of a gas supplied to a gas diffusion layer sample in order to measure the in-plane permeability.

Hereinafter, preferred embodiments of the quality control apparatus for a gas diffusion layer of the present invention will be described in detail referring to FIGS. 1 to 5.

A quality control apparatus for a gas diffusion layer of the present invention comprises a support 20, at least one first pressure device, a plate 10, a first controller 48, a thickness gauge 44, a gas supply controller 58, a connector, a gas supply source and a pressure gauge 54.

The support 20 supports various components of the quality control apparatus. It may be a plate supported by a supporting column 21, as illustrated in FIG. 1, but it may also be formed integrally with the column. In FIG. 1, the support 20 is in the form of a rectangular plate. However, it may have any form as long as it is able to support the various components of the quality control apparatus.

Figure 2:
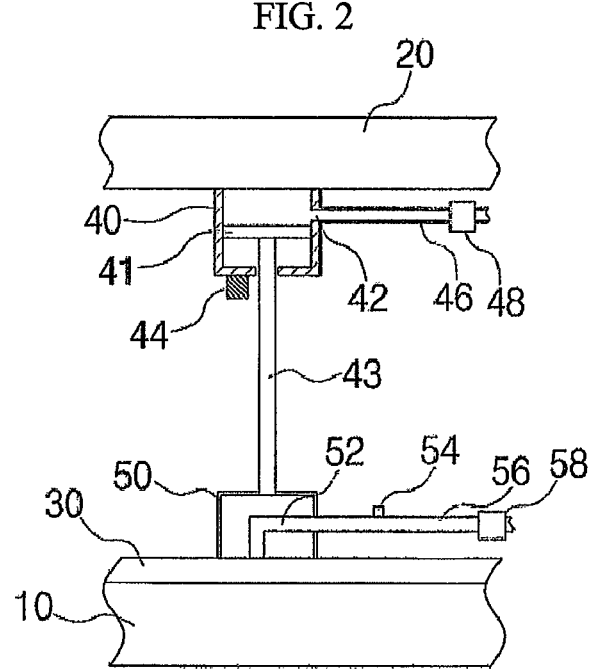
FIG. 2 is a vertical cross-sectional view of a first pressure device of a quality control apparatus for a gas diffusion layer according to an embodiment of the present invention.

The first pressure device is provided at the support 20 and comprises a sample compressing portion 50 compressing a gas diffusion layer sample 30 therebelow. Referring to FIGS. 1 and 2, the first pressure device comprises a first pneumatic cylinder 40 provided at the support 20 and the sample compressing portion 50, which is connected to a piston rod 43 of the first pneumatic cylinder and moves downward as the first pneumatic cylinder is compressed to compress the gas diffusion layer sample 30 therebelow.

The number of the first pressure device may vary depending on the area of the gas diffusion layer sample to be inspected and the configuration of the entire apparatus. If a gas diffusion layer for a fuel cell of vehicles having an active area of approximately 300 cm$^2$ is inspected, it may be preferred that three to five pressure devices are provided.

Figure 3:
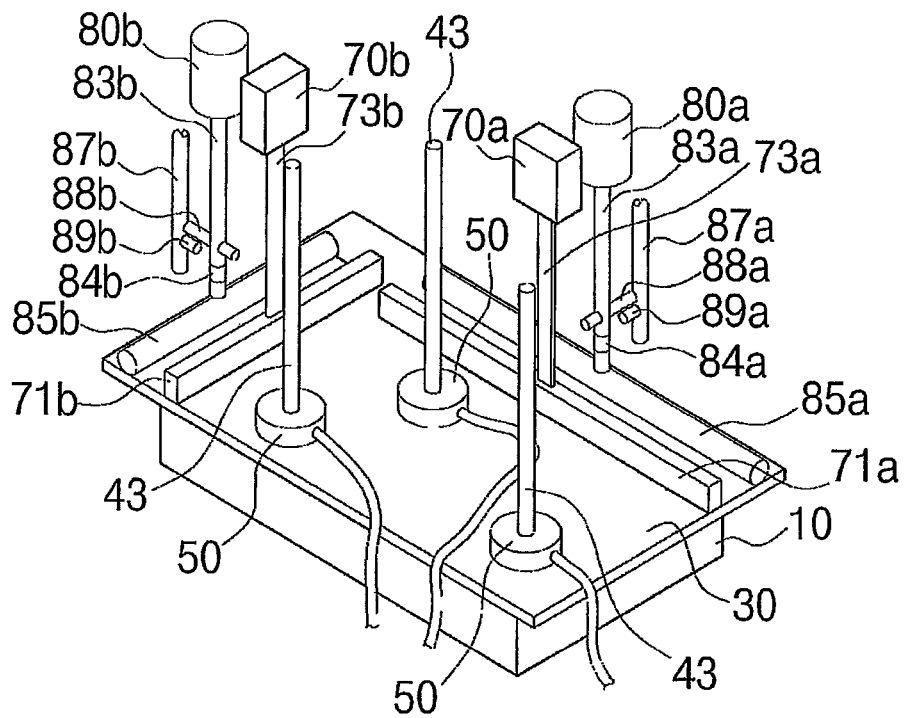
FIG. 3 is a partial perspective view of a quality control apparatus for a gas diffusion layer according to an embodiment of the present invention.
Figure 4:
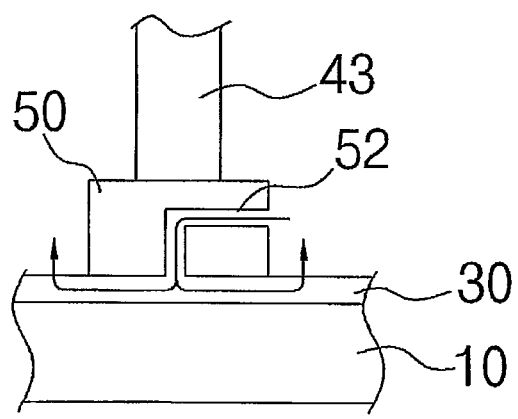
FIG. 4 is a cross-sectional view of a quality control apparatus for a gas diffusion layer according to an embodiment of the present invention, illustrating a flow of a gas discharged to a gas diffusion layer sample through a flow channel.

When the gas diffusion layer sample 30 is placed on the plate 10 or moved, the sample compressing portion 50 may be moved upward by the operation of the pneumatic cylinder 40 so that the gas diffusion layer sample may be easily placed on the plate or moved. In FIGS. 1 to 3, the sample compressing portion 50 is in the form of a cylinder. However, it may have various shapes, including square column or hemisphere, as long as it is able to compress the gas diffusion layer sample with its bottom surface.

Preferably, the compressing portion may be made of a metal material, but any material may be used as long as the compression is performed easily.

In the preferred embodiment illustrated in FIGS. 1 to 3, a pneumatic cylinder was employed for the first pressure device. However, a motor may also be used. The power source for operation may be selected variously by those skilled in the art.

The first controller 48 is connected to the first pneumatic cylinder and controls the air pressure of the first pneumatic cylinder. If the first pressure device is plural, the pneumatic cylinder will be plural. Each pneumatic cylinder may be a hose 46 or a manifold connected via pipes or the like to a hose, which may be connected to the first controller 48. Preferably, the first controller 48 may be a variable pressure regulator (not shown in the figure). It controls the air pressure of the pneumatic cylinder of the first pressure device so that the plurality of compressing portions compress the gas diffusion layer sample with the same pressure.

The thickness gauge 44 attached to the bottom surface of the first pneumatic cylinder 40 measures the thickness of the gas diffusion layer sample. The thickness gauge measures the change of length (thickness) in response to the applied pressure. To describe in detail, the thickness gauge 44 measures the thickness of the gas diffusion layer sample and the change thereof by sensing the displacement of the piston rod 43. The thickness gauge 44 may be a linear voltage displacement transducer (LVDT) type or other displacement type sensor.

To describe in more detail, the thickness of the gas diffusion layer is measured as follows.

1) The thickness of the gas diffusion layer sample at a predetermined pressure is measured according to DIN 53855. In accordance with DIN 53855, the thickness at a pressure of 25 kPa is considered as the initial thickness.

2) When a sufficient pressure, preferably a pressure higher than the value predetermined to compress the sample, is applied without placing the gas diffusion layer sample, the sample compressing portion moves downward and touches the plate, and the position of the piston rod is displayed on the gauge.

3) The gauge value at this time is set to zero.

4) When the variable pressure regulator removes the pressure applied to the pneumatic piston, the sample compressing portion moves upward.

5) The gas diffusion layer sample is placed on the plate 10.

6) When a load of 25 kPa is applied, the thickness of the sample is displayed on the gauge.

7) Then, a wanted pressure is applied and the change of the thickness is measured.

As such, the small change of several μm may be accurately and easily measured using the thickness gauge.

In a preferred embodiment of the present invention, the thickness of the gas diffusion layer sample is measured while the gas diffusion layer sample is compressed with a pressure lower than that applied to a fuel cell stack. Preferably, the thickness of the gas diffusion layer sample is measured while a pressure of about 10 atm or lower is applied by the pressure device.

The plate 10 is provided below the first pressure device and supports the pressure applied to the gas diffusion layer sample. Although not shown in FIG. 1, the plate 10 may have fixing legs. In a preferred embodiment of the present invention, the thickness and the input pressure, which is required to calculate the in-plane permeability, of the gas diffusion layer sample are measured simultaneously while the pressure device compresses the gas diffusion layer sample.

In a preferred embodiment of the present invention, a flow channel 52 is formed in the sample compressing portion 50 to discharge a gas to the gas diffusion layer sample 30. The inlet of the flow channel is formed on the upper surface or side surface of the sample compressing portion 50 and the outlet of the flow channel is formed on the bottom surface of the sample compressing portion 50 to discharge the gas to the gas diffusion layer sample.

In order to supply the gas to the flow channel 52, a connector 56 such as a hose, a pipe, etc. is connected to the inlet of the flow channel. Preferably, in case the pressure device is plural, a plurality of hoses connected to the inlet of the flow channel 52 formed at the plurality of sample compressing portions 50 may form a manifold connected to a hose, which may be connected to the gas supply controller 58.

The gas supply source (not shown in the figure) is connected to the gas supply controller 58 to supply the gas to the flow channel. The gas supply controller 58 controls to consistently supply the gas to the flow channel at a predetermined flow rate and preferably is a variable flow rate regulator. The gas supplied by the gas supply source flows through the flow channel and is discharged to the gas diffusion layer through the outlet. Then, after passing through the gas diffusion layer sample in the transverse direction, the gas is discharged to the upper side of the gas diffusion layer sample. The flow of the gas is represented by arrows in FIG. 4.

The discharge pressure of the gas discharged from the gas diffusion layer sample is equal to the atmospheric pressure. The pressure gauge 54 is provided near the inlet of the flow channel 52 and measures the difference of the input pressure and the discharge pressure.

In order to compute the in-plane permeability, the pressure difference, i.e. the difference of the pressure of the gas before passing through the gas diffusion layer sample in the transverse direction and the atmospheric pressure after passing through the sample, should be measured.

The pressure gauge 54 measures the input pressure of the supplied gas and measures the pressure difference from the atmospheric pressure. Hence, the in-plane permeability may be computed therefrom.

The gas permeability is calculated from Darcy's law.

In case the gas diffusion layer to be measured is coated with a microporous layer, the gas diffusion layer sample should be placed such that the microporous layer faces downward. That is, the in-plane permeability can be measured when the microporous layer of the gas diffusion layer sample faces the plate 10.

In a preferred embodiment of the present invention, a bending stiffness measurer measuring the bending stiffness of the gas diffusion layer sample may be further provided.

The bending stiffness measurer comprises: two fixing devices provided respectively along transverse and longitudinal directions at the support 20 and fixing the gas diffusion layer sample 30 therebelow by compressing; two second pressure devices provided at the support 20 and comprising rods compressing the end portions of the gas diffusion layer sample 30; and load cells 84a, 84b fixed on the rods and measuring a force applied to the rods.

The fixing devices comprise third pneumatic cylinders 70a, 70b provided at the support 20 and fixing portions 71a, 71b which are connected to piston rods 73a, 73b of the third pneumatic cylinders 70a, 70b and move downward as they are compressed and compress the gas diffusion layer sample 30. The fixing device along the transverse direction comprises the fixing portion 71a which moves downward as it is compressed and fixes the gas diffusion layer sample by compressing it in the transverse direction, and the fixing device along the longitudinal direction comprises the fixing portion 71b which moves downward as it is compressed and fixes the gas diffusion layer sample by compressing it in the longitudinal direction. The fixing of the gas diffusion layer sample by the fixing portions 71a, 71b is accomplished by support from the plate 10. In a preferred embodiment of the present invention, the fixing portions 71a, 71b move pneumatically. However, they may also be operated by a motor.

The second pressure devices comprise second pneumatic cylinders 80a, 80b provided at the support 20 and rods 85a, 85b which are connected to piston rods 83a, 83b of the second pneumatic cylinders and move downward as the second pneumatic cylinders are compressed to apply force to the gas diffusion layer sample 30 therebelow.

One rod 85a of the two second pressure devices, i.e. the second pressure device arranged in the transverse direction, is aligned in parallel with the fixing portion 71a in the transverse direction on the plate, and moves downward as it is compressed so that the gas diffusion layer sample is bent within a predetermined angle so as to measure the bending stiffness of the gas diffusion layer sample in the longitudinal direction. The gas diffusion layer sample is partly exposed out of the plate by a predetermined length, and the fixing portion 71a compresses gas diffusion layer sample near the edge of the plate to fix the gas diffusion layer sample by the supporting of the plate 10.

The other rod 85b of the two second pressure devices, i.e. the second pressure device arranged in the longitudinal direction, is aligned in parallel with the fixing portion 71b in the longitudinal direction on the plate, and moves downward as it is compressed so that the gas diffusion layer sample is bent within a predetermined angle so as to measure the bending stiffness of the gas diffusion layer sample in the transverse direction. The gas diffusion layer sample is partly exposed out of the plate by a predetermined length, and the fixing portion 71b compresses gas diffusion layer sample near the edge of the plate to fix the gas diffusion layer sample by the supporting of the plate 10.

The bending stiffness is the force applied to the sample when the sample is bent with a predetermined angle by the downward compression, and should be measured in the two perpendicular directions (transverse and longitudinal directions).

In a preferred embodiment of the present invention, the angle may be 7.5° or 15°.

Figure 5:
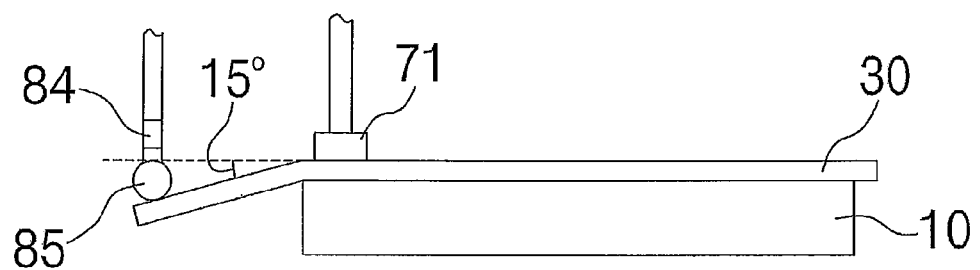
FIG. 5 is a partial view of a quality control apparatus for a gas diffusion layer according to an embodiment of the present invention, illustrating a gas diffusion layer sample bent by an angle of 15° for the measurement of bending stiffness.

FIG. 5 shows the gas diffusion layer sample bent by an angle of 15° by the rods 85a, 85b while it is fixed by the fixing portions 71a, 71b. The load cells 84a, 84b measure the force applied to the sample when the gas diffusion layer sample is bent with the predetermined angle. The load cell is a transducer that converts force into an electrical signal, and may be a strain gauge, a piezoelectric load cell, a vibrating wire load cell, or the like.

Preferably, fixing portions 71a, 71b and the rods 85a, 85b may have the shape of a long rod. Preferably, the fixing portions 71a, 71b and the rods 85a, 85b have a shape that minimizes the damage to the gas diffusion layer sample. For example, the fixing portions 71a, 71b and the rods 85a, 85b may have a shape of a long cylinder.

The third pneumatic cylinders 70a, 70b and the second pneumatic cylinders 80a, 80b are respectively provided with a third controller (not shown in the figure) and a second controller (not shown in the figure) so as to control the air pressure of the third and second pneumatic cylinders. Preferably, the third controller and the second controller are a pressure regulator (not shown in the figure).

Stoppers 89a, 89b and protrusions 88a, 88b of the second pneumatic piston rods are provided so that the second pressure device may compress the gas diffusion layer sample within the predetermined angle. Stopper supports 87a, 87b are provided at the support and the protruding stoppers 89a, 89b are formed on or attached to the stopper supports. Together with the protrusions 88a, 88b of the second pneumatic piston rods, the stoppers restrict the second pressure device so that the second pressure device may compress the gas diffusion layer sample within the predetermined angle.

The second pressure device may compress the gas diffusion layer sample so that the gas diffusion layer sample is bent with the predetermined angle.

In a preferred embodiment of the present invention, a central controller (not shown in the figure) electrically connected to the first controller 48, the gas supply controller 58, the second controller, the third controller, the thickness gauge 44, the pressure gauge 54 and the load cell 84 may be provided. The central controller controls the compression of the first pressure device, the flow rate of the gas permeating the gas diffusion layer sample, the fixing of the fixing device and the force applied to the rod of the second pressure device. Also, it classifies the gas diffusion layer sample depending on the thickness of the gas diffusion layer sample measured by the thickness gauge, computes the in-plane permeability from the pressure measured by the pressure gauge, and displays the bending stiffness of the gas diffusion layer sample by receiving an electrical signal from the load cell.

In another embodiment of the present invention, the thickness gauge may be arranged otherwise. An extending member formed integrally with the plate 10 or extending in the transverse direction by a connecting member is provided. Also, a gauge support extending perpendicularly from each of the sample compressing portions in the transverse direction and bending vertically toward the extending member is provided. To the gauge support, a thickness gauge capable of measuring the thickness of the gas diffusion layer sample while it is compressed is fixed. Other aspects are the same as described in the foregoing preferred embodiments of the present invention.

While the present invention has been described with respect to the specific embodiments, it will be apparent to those skilled in the art that various changes and modifications may be made without departing from the spirit and scope of the invention as defined in the following claims.

What is claimed is:

1. A quality control apparatus for a gas diffusion layer, comprising:
a support;
at least one first pressure device provided at the support and comprising a sample compressing portion compressing a gas diffusion layer sample there below;
a plate provided below the at least one first pressure device and supporting the pressure applied to the gas diffusion layer sample;
a first controller connected to the at least one first pressure device and controlling the compression of the at least one first pressure device;
a thickness gauge attached on one side of the at least one first pressure device and measuring the thickness of the gas diffusion layer sample;
a flow channel formed in the sample compressing portion to discharge a gas to the gas diffusion layer sample;
a gas supply controller connected to the flow channel and controlling to continuously supply the gas to the flow channel at a predetermined flow rate;
a connector connecting the flow channel and the gas supply controller;
a gas supply source connected to the gas supply controller and supplying the gas to the flow channel; and
a pressure gauge measuring an input pressure of the gas diffusion layer sample,
wherein the sample compressing portion moves downward under the control of the first controller and compresses the gas diffusion layer sample placed on the plate, and the inlet of the flow channel is formed on the upper surface or side surface of the sample compressing portion and the outlet of the flow channel is formed on the bottom surface of the sample compressing portion to discharge the gas to the gas diffusion layer sample, and
wherein the at least one first pressure device comprises a first pneumatic cylinder provided at the support and the sample compressing portion, which is connected to a piston rod of the first pneumatic cylinder and moves downward as the first pneumatic cylinder is compressed to compress the gas diffusion layer sample there below,
the first controller is a variable pressure regulator connected to the first pneumatic cylinder and controlling the air pressure of the first pneumatic cylinder, and the thickness gauge is attached below the first pneumatic cylinder and measures the thickness of the gas diffusion layer sample, and wherein two fixing devices provided respectively along transverse and longitudinal directions at the support and fixing the gas diffusion layer sample there below by compressing a third controller connected to the fixing devices and controlling the compression of the fixing devices;

two second pressure devices provided at the support and comprising rods compressing the end portions of the gas diffusion layer sample;

a second controller connected to the second pressure device and controlling the compression of the second pressure device;

a stopper provided at a stopper support provided at the support and restricting the second pressure device so as to compress the gas diffusion layer sample within a predetermined angle;

a protrusion provided at the second pressure device and restricting the downward movement of the second pressure device along with the stopper; and a load cell fixed on the rod and measuring a force applied to the rod, wherein the fixing device along the transverse direction comprises a fixing portion which moves downward as it is compressed and fixes the gas diffusion layer sample by compressing it in the transverse direction, the fixing device along the longitudinal direction comprises a fixing portion which moves downward as it is compressed and fixes the gas diffusion layer sample by compressing it in the longitudinal direction, the fixing of the gas diffusion layer sample by the fixing portion is accomplished by supporting of the plate, one rod of the two second pressure devices is aligned in parallel with the fixing portion in the transverse direction on the plate, the other rod of the two second pressure devices is aligned in parallel with the fixing portion in the longitudinal direction on the plate, and the rods of the second pressure device move downward as they are compressed so that the gas diffusion layer sample is bent within a predetermined angle so as to measure the bending stiffness of the gas diffusion layer sample in the transverse and longitudinal directions.

2. The quality control apparatus for a gas diffusion layer according to claim 1, wherein the connector is a hose one end of which being connected to the inlet of the flow channel, and the gas supply controller is a variable flow rate regulator provided at the other end of the hose and controlling to continuously supply the gas to the flow channel at a predetermined flow rate.

3. The quality control apparatus for a gas diffusion layer according claim 1, wherein the fixing device comprises a third pneumatic cylinder provided at the support and the fixing portion having a shape of a long rod, which is arranged in the transverse or longitudinal direction at the edge portion of the plate, is connected to a piston rod of the third pneumatic cylinder, and moves downward as the third pneumatic cylinder is compressed to fix the gas diffusion layer sample by compressing, and the second pressure device comprises a second pneumatic cylinder provided at the support and a rod which is connected to a piston rod of the second pneumatic cylinder and moves downward as the second pneumatic cylinder is compressed to compress the edge portion of the gas diffusion layer sample.

4. The quality control apparatus for a gas diffusion layer according to claim 3, which further comprises:
a central controller electrically connected to the first controller, the gas supply controller, the second controller, the third controller, the thickness gauge, the pressure gauge and the load cell,
wherein the central controller controls the compression of the first pressure device, the flow rate of the gas permeating the gas diffusion layer sample, the fixing of the fixing device and the force applied to the rod of the second pressure device, classifies the gas diffusion layer sample depending on the thickness of the gas diffusion layer sample measured by the thickness gauge, computes the in-plane permeability from the pressure measured by the pressure gauge, and displays the bending stiffness of the gas diffusion layer sample by receiving an electrical signal from the load cell.

* * * * *